(12) United States Patent
Sugiyama et al.

(10) Patent No.: US 6,787,325 B1
(45) Date of Patent: Sep. 7, 2004

(54) COMPLEXES CONTAINING CROSSLINKED AVIDIN, ANALYTICAL METHOD WITH THE USE OF CROSSLINKED AVIDIN AND ANALYTICAL REAGENTS AND KITS

(75) Inventors: Kazuyuki Sugiyama, Tokyo (JP); Nobuhiro Hoshino, Tokyo (JP); Hiroki Tatsumi, Chiba (JP); Satoshi Fukuda, Chiba (JP)

(73) Assignees: Iatron Laboratories, Inc., Tokyo (JP); Kikkoman Corporation, Chiba (JP)

( * ) Notice: Subject to any disclaimer, the term of this patent is extended or adjusted under 35 U.S.C. 154(b) by 0 days.

(21) Appl. No.: 09/582,842

(22) PCT Filed: Nov. 5, 1999

(86) PCT No.: PCT/JP99/06172

§ 371 (c)(1),
(2), (4) Date: Jul. 5, 2000

(87) PCT Pub. No.: WO00/28326

PCT Pub. Date: May 18, 2000

(30) Foreign Application Priority Data

Nov. 6, 1998 (JP) .......................................... 10-316172

(51) Int. Cl.[7] ............................................... C12Q 1/66
(52) U.S. Cl. .............................. 435/8; 435/7.5; 435/7.6; 435/7.7; 435/7.72; 435/7.71; 435/7.8; 435/975; 435/7.37; 435/21; 435/23; 436/540; 436/542; 436/545; 436/546; 436/504; 436/512
(58) Field of Search ............................. 435/8, 7.5, 7.6, 435/7.7, 7.72, 7.71, 7.8, 975, 7.92–7.95, 21, 23, 7.37; 436/545, 540, 542, 546, 504, 512

(56) References Cited

U.S. PATENT DOCUMENTS

| | | | | |
|---|---|---|---|---|
| 4,228,237 A | * | 10/1980 | Hevey et al. .................... | 435/7 |
| 4,478,914 A | * | 10/1984 | Giese | |
| 4,778,751 A | * | 10/1988 | El Shami et al. ................ | 435/7 |
| 5,443,986 A | * | 8/1995 | Haughland et al. ............. | 435/4 |
| 5,482,698 A | * | 1/1996 | Griffiths ....................... | 424/141 |
| 5,589,342 A | * | 12/1996 | Geiger et al. ................... | 435/6 |
| 5,698,405 A | * | 12/1997 | Goldenberg ................. | 435/7.5 |
| 5,843,746 A | * | 12/1998 | Tatsumi et al. .............. | 435/189 |
| 5,846,727 A | * | 12/1998 | Soper et al. .................... | 435/6 |
| 5,869,232 A | * | 2/1999 | Sallberg ......................... | 435/5 |
| 5,880,270 A | * | 3/1999 | Berninger et al. ........ | 530/391.1 |
| 5,916,750 A | * | 6/1999 | Iyer et al. ....................... | 435/6 |
| 5,973,124 A | * | 10/1999 | Bayer et al. ................. | 530/402 |
| 5,976,878 A | * | 11/1999 | Boyce ........................ | 435/366 |
| 6,010,867 A | * | 1/2000 | Kobayashi et al. ........... | 435/7.5 |
| 6,022,951 A | * | 2/2000 | Sano et al. ................... | 530/350 |
| 6,054,266 A | * | 4/2000 | Kronick et al. ................ | 435/6 |
| 6,130,323 A | * | 10/2000 | Su et al. ..................... | 536/23.1 |

FOREIGN PATENT DOCUMENTS

| | | | | |
|---|---|---|---|---|
| EP | 0328372 A2 | * | 8/1989 | .......... G01N/33/68 |
| JP | 59-142466 | | 8/1984 | |
| JP | 3-128460 | | 5/1991 | |
| JP | 8-308578 | | 11/1996 | |
| JP | 200146965 | * | 5/2000 | .......... G01N/33/531 |

OTHER PUBLICATIONS

Nature Biotechnology, vol. 14, No. 8 (1996) p. 1007–1011.
International Search Report.

* cited by examiner

Primary Examiner—Christopher L. Chin
Assistant Examiner—Pensee T. Do
(74) Attorney, Agent, or Firm—Sughrue Mion, PLLC

(57) ABSTRACT

Provided are novel complexes containing a crosslinked avidin, an analyzing method and analyzing reagents and kits whereby a compound to be analyzed can be quickly, conveniently and accurately analyzed while taking advantage of the avidin-biotin reaction. The complexes contain at least two homogeneous or heterogeneous biotin-introduced products and one crosslinked avidin sandwiched therebetween. In the analyzing method, the homogeneous or heterogeneous biotin-introduced products and the crosslinked avidin are used. The analyzing reagent contains the crosslinked avidin. The analyzing kit contains the crosslinked avidin and a biotinylating agent.

17 Claims, 2 Drawing Sheets

COMPLEXES CONTAINING CROSSLINKED AVIDIN, ANALYTICAL METHOD WITH THE USE OF CROSSLINKED AVIDIN AND ANALYTICAL REAGENTS AND KITS

This application is a 371 of PCT/JP99/06172 filed on Nov. 5, 1999 and claims foreign priority to Japan 10-316172 filed on Nov. 6, 1998.

TECHNICAL FIELD

The present invention relates to a novel complex containing a crosslinked avidin, a method for preparing the novel complex, an analyzing method using the crosslinked avidin, an analyzing reagent, and an analyzing kit. The term "analyzing" or "analysis" as used herein includes a detection used to determine the presence or absence of a compound to be analyzed, and a quantitative determination of an amount of a compound to be analyzed.

BACKGROUND ART

An enzyme immunoassay is a highly sensitive assay making use of an antigen-antibody reaction. A typical enzyme immunoassay is a heterogeneous enzyme immunoassay, such as a sandwich method, wherein an antibody immobilized on a solid phase and a labeled antibody are used, or a competitive method wherein the solid phase-immobilized antibody and a labeled antigen are used.

An enzyme-labeled antigen or an enzyme-labeled antibody used in the above assays is prepared by various methods. For example, in an early stage there was developed a method for randomly preparing a polymer of enzymes and antigens or antibodies by adding glutaraldehyde having a bivalent reactivity to a mixture of the enzymes and antigens or antibodies. Thereafter, an improvement was attempted to make use of the fact that peroxidase has a small number of amino groups on the surface thereof, and exhibits a strong resistance to a chemically reactive reagent. More particularly, an improved method for synthesizing only the desired enzyme-labeled antibodies by reacting glutaraldehyde with peroxidase, removing excess aldehyde groups, and mixing the resulting aldehyde-introduced peroxidase with antibodies was developed. Further, a method for producing enzyme-labeled antibodies in a high yield was developed in view of the fact that peroxidase has sugar chains. Specifically, this method comprises oxidizing sugar chains with periodic acid to form aldehyde groups, and binding amino groups of antibodies thereto to produce enzyme-labeled antibodies.

Various crosslinking agents were developed and used in reactions binding antibodies and enzymes. Of these crosslinking agents, a heterobifunctional crosslinking agent having a succinimide group and a maleimide group at both ends was developed. This agent can specifically link an amino group of an enzyme to an SH group in a hinge region of an antibody to produce an enzyme-labeled antibody in a high yield.

Besides the above methods, wherein an antigen or an antibody is bound to an enzyme with a crosslinking agent, coupling methods using an avidin-biotin reaction to bind an antigen or an antibody to an enzyme were developed. In these methods, a combination of two reagents is generally used. More particularly, on one hand, a biotinylating agent is used to prepare an antigen or antibody to which a biotin is introduced, i.e., a biotin-introduced antigen or a biotin-introduced antibody. On the other hand, (1) a complex of an enzyme and an avidin, i.e., an enzyme-labeled avidin, is prepared by a chemically binding method, or (2) a complex of an enzyme and an avidin via a biotin, i.e., an enzyme-labeled avidin, is prepared by mixing a biotin-introduced enzyme and an avidin in a suitable ratio.

The chemically binding method (1) comprises binding an enzyme and an avidin with glutaraldehyde or a heterobifunctional crosslinking agent, and thus can be performed by repeating a procedure of the method for preparing the enzyme-labeled antibody, except that an enzyme and avidin are combined instead of the combination of an enzyme and an antibody.

The biotin-introduced enzyme used in the above method (2) can be prepared, for example, in accordance with a gene manipulation technique, when luciferase is used as an enzyme. Specifically, when a gene containing a luciferase gene and a biotin acceptor gene ligated thereto is expressed in a host cell, a luciferase-biotin acceptor fused protein is synthesized in the host cell. Then, biotin is coupled with the fused protein by an action of the host cell to produce a biotin-introduced enzyme, i.e., a luciferase-biotin acceptor fused protein to which biotin is introduced.

The method wherein the resulting biotin-introduced antigen or biotin-introduced antibody and the enzyme-labeled avidin are used comprises reacting a sample containing a compound (an antigen) to be analyzed with a carrier carrying immobilized antibodies thereon; washing the reaction mixture; reacting the biotin-introduced antibody therewith; washing the reaction mixture; reacting the enzyme-labeled avidin therewith, and measuring an amount of the enzyme stemming from the enzyme-labeled avidin bound to the complex of the immobilized antibodies-carrying carrier and the compound to be analyzed, whereby an amount of the antigen can be determined.

The immunoassay using the avidin-biotin reaction has advantages in that, if the enzyme-labeled avidin is prepared in advance, various antibodies may be used as a label after biotinylation, and in that an enzyme whose activity is heavily damaged by a chemical treatment may be used in the form of an enzyme-labeled avidin while maintaining its activity, if the biotin-introduced enzyme is expressed in accordance with the gene manipulation. However, the above immunoassay has disadvantages in that the number of process steps is increased and data obtained in each determination shows a poorer reproducibility.

An attempt to reduce the reaction steps was made by premixing a biotin-introduced antibody, avidin, and a biotin-introduced enzyme and using them in the form of an enzyme-labeled antibody, i.e., a biotin-introduced antibody-avidin-biotin-introduced enzyme complex. However, the reactivity is greatly lowered, or stability is remarkably reduced, and therefore, it cannot be used as a reagent as it is.

The avidin-biotin reaction is applied, besides the immunoassay, to a DNA or RNA assay by a DNA probe, or a receptor-ligand assay. The application of the avidin-biotin reaction to the above assays has disadvantages similar to those encountered in the immunoassays.

Accordingly, the object of the present invention is to remedy the above-mentioned disadvantages of the prior art, and to provide a quick, convenient and accurate assay having a small number of procedure steps.

DISCLOSURE OF INVENTION

The present invention relates to a biotin-avidin-biotin complex comprising at least two biotin-introduced products which are the same or different, and a crosslinked avidin sandwiched therebetween.

In the biotin-avidin-biotin complex of the present invention, at least one of the biotin-introduced products is preferably a biotin-introduced binding component, and at least one of the biotin-introduced products is preferably a biotin-introduced labeling substance.

Further, the present invention relates to a process for preparing the biotin-avidin-biotin complex, comprising the steps of:
(1) treating an avidin with a crosslinking agent to prepare a crosslinked avidin,
(2) biotinylating the same or different substances to be biotinylated to prepare the same or different biotin-introduced products; and
(3) binding the crosslinked avidin and the same or different biotin-introduced products to form the biotin-avidin-biotin complex.

Further, the present invention relates to an analyzing method characterized in that biotin-introduced products which are the same or different, and a crosslinked avidin are used.

Further, the present invention relates to an analyzing method characterized in that (1) a biotin-introduced binding component, (2) a crosslinked avidin, and (3) a biotin-introduced labeling substance are used.

Further, the present invention relates to a method for analyzing a compound to be analyzed characterized in that (1) a sample possibly containing the compound to be analyzed, a biotin-introduced binding component capable of binding specifically to the compound to be analyzed, a crosslinked avidin, and a biotin-introduced labeling substance are brought into contact with each other in any sequential order, to form a complex of the compound to be analyzed, the biotin-introduced binding component, the crosslinked avidin, and the biotin-introduced labeling substance; and
(2) analyzing a signal derived from the labeling substance in the complex.

Further, the present invention relates to an analyzing reagent characterized by containing a crosslinked avidin.

Further, the present invention relates to an analyzing kit characterized by containing a crosslinked avidin and a biotinylating agent.

Further, the present invention relates to an analyzing kit characterized by containing
(1) a biotin-introduced binding component,
(2) a crosslinked avidin, and
(3) a biotin-introduced labeling substance.

The term "analyzing" or "analysis" as used herein means a binding analysis wherein the properties of two compounds binding specifically to each other are used, one of the two compounds corresponding to a target compound to be analyzed, and then the target compound is analyzed, using a "binding component" capable of specifically binding to the target compound to be analyzed. As a combination of the two compounds which specifically bind to each other, there may be mentioned a combination of an antigen and an antibody, a combination of a DNA and a DNA or RNA complementary thereto, a combination of an RNA and a DNA or RNA complementary thereto, a combination of a receptor and a ligand thereof, such as a hormone, cytokine, neurotransmitter, or lectin, a combination of an enzyme and a ligand thereof, such as a substrate analogue of the enzyme, a coenzyme, a regulatory factor, or an inhibitor, a combination of an enzyme analogue and a substrate for an enzyme which is an origin of the enzyme analogue, and a combination of a sugar and a lectin. The enzyme analogue is a compound having a high affinity to a substrate of the original enzyme but exhibiting no catalytic activity.

BEST MODE FOR CARRYING OUT THE INVENTION

Figure 1:
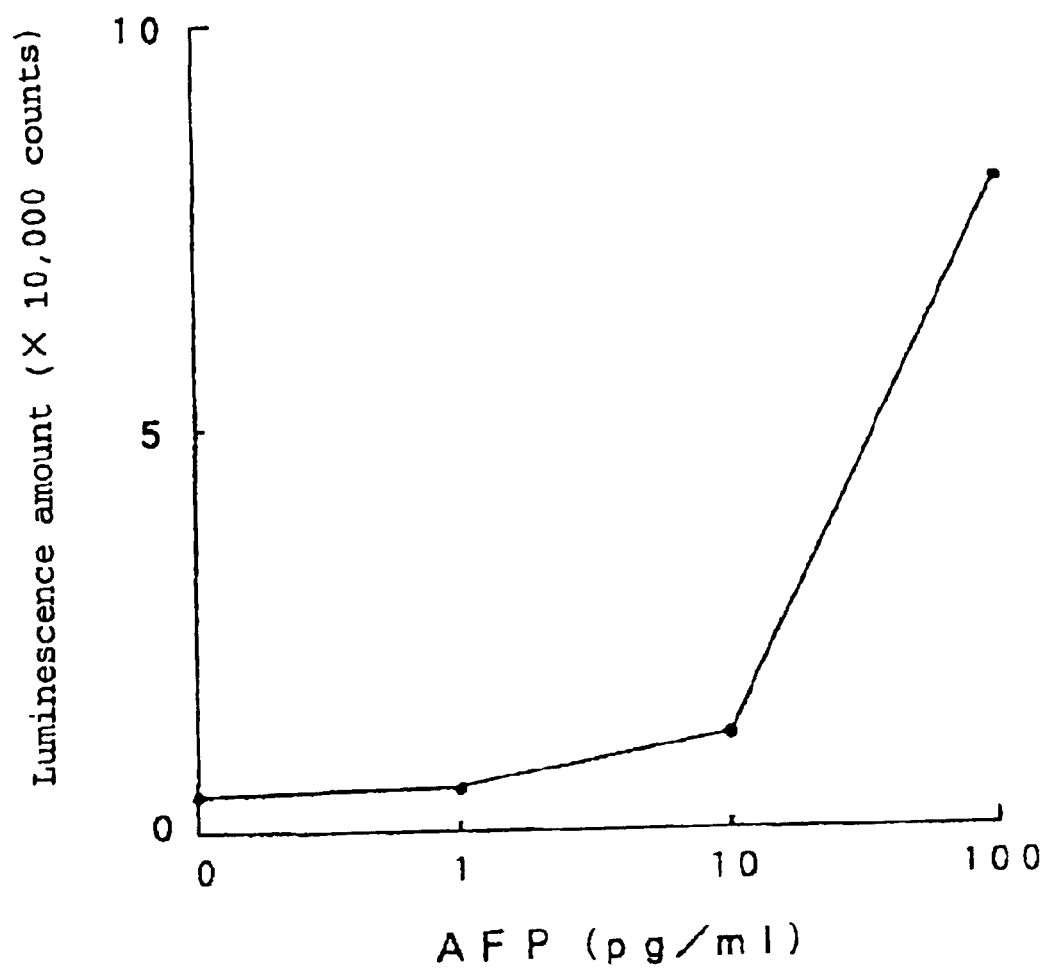
FIG. 1 is a graph showing the results obtained by measuring AFP in accordance with an ELISA using a crosslinked streptoavidin.

The biotin-avidin-biotin complex of the present invention contains two or more biotin-introduced products which are the same as or different from each other, and a crosslinked avidin sandwiched therebetween. The crosslinked avidin is bound to each of biotin-introduced products via a bond of a biotin-avidin reaction.

The avidin which may be used in the present invention is any avidin which will bind to biotin, for example, an egg-white avidin, a streptoavidin, an avidin prepared by a gene manipulation technique, i.e., a recombinant avidin, or the like.

The avidin is a protein composed of four of the same subunits. The subunit has a biotin binding site, and an avidin molecule can bind to 4 biotin molecules. The subunits are not bound to each other via a covalent bond. It is known that when the avidin is heated at an elevated temperature, it is cleaved to each subunit.

In the crosslinked avidin used in the present invention, there exist crosslinkages at least between subunits, i.e., intramolecular crosslinkages. The crosslinked avidin may be a crosslinked avidin monomer composed of an avidin molecule, and a crosslinked avidin polymer composed of plural avidin molecules which are bound to each other by intermolecular crosslinkages.

The crosslinked avidin can be prepared by treating avidin with a crosslinking agent. The crosslinking agent which may be used is, for example, a crosslinking agent for binding two amino groups, such as glutaraldehyde, disuccinimide, dimethylpimelimidate, or dimethylsuberimidate, or a crosslinking agent for binding an amino group and a carboxyl group, for example, various carbodiimides, such as 1-ethyl-3(3-dimethylaminopropyl)carbodiimide.

The biotin-introduced product used in the present invention is prepared by biotinylating any substance to be biotinylated. The substance to be biotinylated is not particularly limited, so long as it can be biotinylated and the resulting biotinylated product will bind to the crosslinked avidin by the biotin-avidin reaction. The substance to be biotinylated may be any substance in a solution, for example, a labeling substance used for labeling an antibody or antigen in a conventional immunoassay, or a binding component which may be biotinylated.

As the labeling substance, there may be mentioned, for example, an enzyme, a fluorescent substance or a fluorescent substance-binding protein, or a luminescent substance or a luminescent substance-binding protein, or a radioactive isotope.

The enzyme may be, for example, luciferase, alkaline phosphatase, peroxidase, β-D-galactosidase, glucokinase, hexokinase, or glucose-6-phosphate dehydrogenase (G6PDH).

The fluorescent substance may be, for example, fluorescein, rhodamine, dansylchloride, fluoronitrobenzofurazane, europium chelate, or samarium chelate.

The fluorescent substance-binding protein may be, for example, a protein to which fluorescent substances are bound and accumulated thereon.

The luminescent substance may be, for example, an acridinium ester, adamantyl-dioxane, or isolumina; and the luminescent substance-binding protein may be, for example, a protein to which luminescent substances are bound and accumulated thereon.

The radioactive isotope may be, for example, $^{32}P$, $^{35}S$, $^{125}I$, or $^{3}H$.

The biotin-introduced enzyme which may be used in the present invention is, for example, a biotinylated enzyme, such as luciferase, alkaline phosphatase, peroxidase, or β-D-galactosidase.

The biotin-introduced enzyme may be prepared, for example, by a chemical modification method or a gene manipulation method. The chemical modification method comprises chemically binding biotin to an amino acid group of an enzyme.

The gene manipulation method comprises expressing a fused protein of an enzyme and a biotin acceptor in a host cell to obtain a biotin-introduced enzyme. The gene manipulation method is preferable for an enzyme, such as luciferase, which is labile to a chemical modification. The biotin acceptor means a protein containing a particular amino acid sequence to which biotin is added in a host cell. A gene containing a sequence encoding the acceptor protein may be selected in accordance with the application thereof.

When a gene containing an enzyme gene (such as a luciferase gene) and a biotin acceptor gene ligated thereto is expressed in a host cell, an enzyme-biotin acceptor fused protein is synthesized in the host cell. Then biotin is bound to the fused protein by the action of the host cell, and thus a biotin-introduced enzyme, i.e., a biotin-introduced enzyme-biotin acceptor fused protein, may be obtained.

Of the biotin-introduced labeling substances which may be used in the present invention, the substances other than the biotin-introduced enzyme may be prepared according to methods which are in themselves known.

The binding component in the biotin-introduced binding component which may be used in the present invention is not particularly limited, so long as it may be biotinylated, and can bind specifically to a compound to be analyzed. As the binding component, there may be mentioned, for example, (a) a protein, such as an antibody which may be a monoclonal antibody or a polyclonal antibody, an antibody fragment [such as, Fab, Fab', F(ab')$_2$, or Fv], a protein antigen, a receptor, a protein hormone, a cytokine, a lectin, an enzyme, or an enzyme analogue; (b) a nucleic acid such as a DNA or an RNA; or (c) a compound other than a protein or a nucleic acid, such as a nonprotein antigen, a nonprotein hormone, a ligand to an enzyme (such as a substrate analogue to an enzyme, a coenzyme, a transcription factor, or an inhibitor), a substrate of an original enzyme of an enzyme analogue, or a sugar.

The biotin-introduced binding component which may be used in the present invention and contains the protein binding component (such as an antibody, an antibody fragment, a protein antigen, a receptor, a protein hormone, a cytokine, a lectin, an enzyme, or an enzyme analogue) may be prepared by introducing biotin into the binding component according to the methods described in connection with the biotin-introduced enzyme, i.e., the chemical modification method or the gene manipulation method.

The biotin-introduced binding component which may be used in the present invention and contains the nucleic acid binding component (such as a DNA or an RNA) may be prepared by introducing biotin into the binding component according to methods which are in themselves known. The known methods are, for example, a method wherein a nick translation or a primer elongation is carried out under the condition that one of four nucleotides is replaced with a biotinylated nucleotide, such as a biotinylated dUTP or a biotinylated UTP, or a method wherein a DNA synthesis is carried out under the condition that one of four nucleotides is replaced with an aminated nucleotide, such as an amino-7-dUTP, and the resulting modified DNA is reacted with a suitable biotin derivative.

As the biotinylated dUTP or the biotinylated UTP which is used in the nick translation or the primer elongation, for example, a nucleotide containing biotin bound to 5-carbon atom in the pyrimidine ring of dUTP or UTP via a linker is commercially available, and thus can be used.

The biotin-introduced binding component which may be used in the present invention and contains the compound other than a protein or a nucleic acid may be prepared by introducing biotin into the binding component according to methods which are in themselves known.

A combination of the biotin-introduced products in the biotin-avidin-biotin complex of the present invention is not particularly limited, so long as the complex contains at least two biotin-introduced products which may be the same as or different from each other, and one crosslinked avidin sandwiched therebetween. The combination may be, for example, a combination of a biotin-introduced binding component and a biotin-introduced labeling substance, a combination of a biotin-introduced binding component and a same or different biotin-introduced binding component, or a combination of a biotin-introduced labeling substance and a same or different biotin-introduced labeling substance. The combination of the biotin-introduced binding component and the biotin-introduced labeling substance is preferable.

A preferable biotin-introduced binding component used in the present invention contains one biotin in a molecule, that is, a biotin molecule per a binding component molecule. In a preferable embodiment of the present invention, a biotin-introduced antibody fragment Fab' may be used as the biotin-introduced binding component. The biotin-introduced antibody fragment Fab' may be prepared by covalently introducing a biotin molecule into an antibody fragment Fab' obtained from an antibody (which may be a monoclonal antibody or a polyclonal antibody) specifically binding to a compound to be analyzed.

The antibody fragment Fab' may be prepared by digesting an antibody with pepsin, and reducing the resulting antibody fragment F(ab')$_2$ with a reducing agent, such as β-mercaptoethanol or mercaptoethyl amine. More particularly, there exists an S—S bond connecting two heavy chains in the hinge region of an antibody molecule. The digestion with pepsin occurs downstream of the S—S bond on the C-terminus, and thus the S—S bond remains in the C-terminal region of the antibody fragment F(ab')$_2$. When the S—S bond is reduced with the reducing agent, two molecules of an antibody fragment Fab' are formed from a molecule of the antibody fragment F(ab')$_2$. The resulting antibody fragment Fab' contains an SH group in the C-terminal region, respectively.

The biotin-introduced antibody fragment Fab' having a biotin molecule per an antibody fragment Fab' molecule may be prepared by reacting the resulting antibody fragment Fab' having an SH group with a biotin derivative having a maleimide group. The biotin-introduced antigen which may be used in the present invention is preferably a product prepared by covalently introducing a biotin molecule into an antigen. The biotin-introduced antigen may be prepared according to the methods described in connection with the biotin-introduced enzyme, that is, the chemical modification method or the gene manipulation method.

The biotin-avidin-biotin complex of the present invention may be prepared according to, but is by no means limited to, for example, the preparing process of the present invention. According to the preparing process of the present invention, the crosslinked avidin, and the same or different biotin-introduced products are separately prepared in advance, and then are coupled concurrently or sequentially to form the biotin-avidin-biotin complex of the present invention.

The biotin-avidin-biotin complex of the present invention may be used, for example, in the analyzing method of the present invention. In the present invention, a suitable biotin-introduced product, particularly a biotin-introduced binding component, can be selected in accordance with a compound to be analyzed. For example, when an antigen is a compound to be analyzed, a biotin-introduced antibody or a biotin-introduced antibody fragment prepared by introducing biotin into an antibody or an antibody fragment specifically reacting to the antigen may be used. When an antibody is a compound to be analyzed, a biotin-introduced antigen prepared by introducing biotin into an antigen recognized by the antibody may be used. When a DNA or RNA is a compound to be analyzed, a biotin-introduced DNA or a biotin-introduced RNA prepared by introducing biotin into a DNA or RNA complementary to the DNA or RNA to be analyzed may be used. When a receptor is a compound to be analyzed, a biotin-introduced ligand prepared by introducing biotin into a ligand of the receptor may be used. When a ligand of a receptor is a compound to be analyzed, a biotin-introduced receptor prepared by introducing biotin into a receptor to the ligand may be used. When an enzyme is a compound to be analyzed, a biotin-introduced ligand prepared by introducing biotin into a ligand to the enzyme may be used. When a ligand of an enzyme is a compound to be analyzed, a biotin-introduced enzyme prepared by introducing biotin into the enzyme may be used.

The present invention, i.e., the analyzing method, the analyzing reagent and the analyzing kit of the present invention, will be further described hereinafter mainly as to the embodiments wherein the biotin-introduced antibody fragment Fab' is used as the biotin-introduced binding component, and the biotin-introduced enzyme is used as the biotin-introduced labeling substance.

For example, the enzyme-labeled antibody may be obtained by mixing, in an appropriate ratio, (1) the biotin-introduced antibody fragment Fab', (2) the crosslinked avidin, and (3) the biotin-introduced enzyme, each prepared in advance according to the above-mentioned method, while maintaining an enzyme activity and an antibody activity.

Further, (1) the biotin-introduced antibody fragment Fab', (2) the crosslinked avidin, and (3) the biotin-introduced enzyme may be used separately. For example, after the antibody-immobilized carrier and a compound (an antigen) to be analyzed are reacted, (a) the above-mentioned three reagents (1) to (3) are added in the sequential order as above to carry out the reactions in three steps, (b) a mixture prepared in advance from the biotin-introduced antibody fragment Fab' and the crosslinked avidin is reacted therewith, and then the biotin-introduced enzyme is reacted, to thereby carry out the reactions in two steps, or (c) the biotin-introduced antibody fragment Fab' is reacted, and then a mixture prepared in advance from the crosslinked avidin and the biotin-introduced enzyme is reacted, to thereby carry out the reactions in two steps.

The manner of use of the above three reagents, i.e., whether the reagents are used after the mixture thereof is formed in advance, or used separately, can be appropriately selected in accordance with a measuring method used.

The analyzing method of the present invention can be applied to a conventional immunoassay, such as a sandwich method or a competitive method, without any modification, except that (1) the biotin-introduced antibody fragment Fab', (2) the crosslinked avidin, and (3) the biotin-introduced enzyme are used.

For example, according to the analyzing method of the present invention wherein the enzyme-labeled antibody prepared by mixing in an appropriate ratio (1) the biotin-introduced antibody fragment Fab', (2) the crosslinked avidin, and (3) the biotin-introduced enzyme is used in the sandwich method, an antibody or an antibody fragment (a first antibody) reacting a compound to be analyzed at an epitope different from that recognized by the biotin-introduced antibody fragment Fab' is immobilized to an appropriate insoluble carrier. Then, a surface of the insoluble carrier is coated with an appropriate blocking agent, such as bovine serum albumin (BSA) or gelatin, to prevent a non-specific binding between the insoluble carrier and a sample. Thereafter, the sample is added to and brought into contact with the first antibody for a predetermined period of time, for example, for 5 minutes to 3 hours, at a predetermined temperature, for example, at 4° C. to 40° C., preferably around room temperature, to perform a reaction (a first reaction). Then, the mixture of the three reagents, i.e., the enzyme-labeled antibody, is added to and brought into contact with the reaction mixture for a predetermined period of time, for example, for 5 minutes to 3 hours, at a predetermined temperature, for example, at 4° C. to 40° C., preferably around room temperature, to perform a reaction (a second reaction). The whole is washed with an appropriate detergent, such as a physiological saline containing a surfactant, and then an amount of the enzyme-labeled antibodies present on the insoluble carrier is quantitatively determined. An amount of the compound to be analyzed in the sample can be calculated from the resulting determinations.

In the analyzing method of the present invention, the three reagents may be added separately to conduct the reactions in two or three steps as above, instead of conducting the reactions in one step by adding the mixture of the three reagents, i.e., the enzyme-labeled antibody.

The subunits in the crosslinked avidin used in the analyzing method of the present invention are covalently bound to each other. Therefore, when the enzyme-labeled antibody is prepared by mixing in an appropriate ratio (1) the biotin-introduced antibody fragment Fab', (2) the crosslinked avidin, and (3) the biotin-introduced enzyme, the enzyme activity and the antibody activity can be stably maintained. On the contrary, a reactivity of the conventional enzyme-labeled antibody containing a non-crosslinked avidin, i.e., a biotin-introduced antibody/avidin/biotin-introduced enzyme complex, is greatly lowered as the enzyme-labeled antibody. The reason for this is presumed to be that when two biotin molecules (a biotin-introduced antibody and a biotin-introduced enzyme) bind to an avidin molecule, a strong stress is imposed on the avidin, as in the case when a high heat is applied, and thus the subunits are cleaved from each other.

Further, when the biotin-introduced antibody fragment Fab' containing a biotin molecule in a molecule thereof is used together with the biotin-introduced enzyme, the enzyme activity and the antibody activity can be more stably maintained. The reason for this is presumed to be that when an antibody fragment Fab', an antigen, or an enzyme contains plural biotin molecules, coupling chain reactions proceed via avidins, macromolecules of the enzyme-labeled antibodies are formed, and undesirable reactions, such as a precipitation, occur.

The analyzing reagent of the present invention contains the crosslinked avidin. Also, the analyzing reagent of the present invention may be used in combination with other reagents, such as the biotin-introduced antibody fragment Fab' and the biotin-introduced enzyme, in the analyzing method of the present invention.

The analyzing kit of the present invention contains the crosslinked avidin and the biotinylating agent. The biotinylating agent which may be used is a conventional biotinylating agent, such as N-biotinoyl-N'-(6-maleimidehexanoyl)-hydrazide, or N-hydroxysuccinimide biotinoyl-$\epsilon$-aminocaproate. In the analyzing reagent of the present invention, a biotin-introduced antibody fragment Fab' and a biotin-introduced enzyme which are prepared by biotinylating, with a biotinylating agent, an antibody fragment Fab' and an enzyme provided apart from the analyzing kit of the present invention may be used in combination with the crosslinked avidin as a component of the analyzing kit of the present invention.

In addition to the crosslinked avidin and the biotinylating agent, the analyzing kit of the present invention may further contain the biotin-introduced labeling substance, such as a biotin-introduced enzyme. The analyzing kit of the present invention may contain the crosslinked avidin, the biotin-introduced labeling substance, and the biotinylating agent as a separate reagent, respectively. Alternatively, the kit may contain these in the form of a mixture of the crosslinked avidin and the biotin-introduced labeling substance, and in the form of a single component of the biotinylating agent.

The analyzing kit of the present invention may contain, instead of the biotinylating agent, the biotin-introduced antibody fragment Fab' and the biotin-introduced labeling substance, such as the biotin-introduced enzyme, as the components thereof. More particularly, another embodiment of the analyzing kit of the present invention contains (1) the biotin-introduced antibody fragment Fab', (2) the crosslinked avidin, and (3) the biotin-introduced labeling substance. The analyzing kit of the present invention may contain (1) the biotin-introduced antibody fragment Fab', (2) the crosslinked avidin, and (3) the biotin-introduced labeling substance, as separate components, or as a mixture of two or more components. Examples of the analyzing kit containing the mixture are an analyzing kit containing a mixture of the biotin-introduced antibody fragment Fab', the crosslinked avidin and the biotin-introduced labeling substance; an analyzing kit containing a mixture of the biotin-introduced antibody fragment Fab' and the crosslinked avidin, and a single component of the biotin-introduced labeling substance; and an analyzing kit containing a single component of the biotin-introduced antibody fragment Fab', and a mixture of the crosslinked avidin and the biotin-introduced labeling substance.

The analyzing kit of the present invention can be used alone or, if desired, as a combination of other reagents, in the analyzing method of the present invention.

Although the present invention is described mainly with respect to the embodiment wherein the biotin-introduced antibody fragment Fab' is used as the biotin-introduced binding component, and the biotin-introduced enzyme is used as the biotin-introduced labeling substance, a biotin-introduced antigen can be used instead of the biotin-introduced antibody fragment Fab' to carry out the present invention.

An embodiment of the present invention wherein the biotin-introduced enzyme is used as the biotin-introduced labeling substance will be described hereinafter.

For example, in the analyzing method of the present invention wherein the enzyme-labeled antigen prepared by mixing in an appropriate ratio (1) the biotin-introduced antigen, (2) the crosslinked avidin, and (3) the biotin-introduced enzyme is used, an antigen can be immunologically analyzed, for example, by a competitive method. More particularly, an antibody or an antibody fragment (a first antibody) reacting a compound to be analyzed is immobilized to an appropriate insoluble carrier. Then, a surface of the insoluble carrier is coated with an appropriate blocking agent, such as bovine serum albumin (BSA) or gelatin, to prevent a non-specific binding between the insoluble carrier and a sample. Thereafter, the sample and the enzyme-labeled antigen, which is the mixture of the three reagents, are added to and brought into contact with the insoluble carrier for a predetermined period of time, for example, for 5 minutes to 3 hours, at a predetermined temperature, for example, at 4° C. to 40° C., preferably around room temperature, to perform a reaction. Then, the whole is washed with an appropriate detergent, such as a physiological saline containing a surfactant, and an amount of the enzyme-labeled antigens present on the insoluble carrier is quantitatively determined. An amount of the compound to be analyzed in the sample can be calculated from the resulting determinations.

In the analyzing method of the present invention, the three reagents may be added separately to conduct the reactions in two or three steps as above, instead of conducting the reactions in one step by adding the mixture of the three reagents, i.e., the enzyme-labeled antigen.

Further, instead of the biotin-introduced antibody fragment Fab' or the biotin-introduced antigen, the present invention can be carried out, using other biotin-introduced binding components, such as a biotin-introduced antibody, a biotin-introduced antibody fragment, a biotin-introduced DNA, a biotin-introduced RNA, a biotin-introduced receptor, a biotin-introduced enzyme, a biotin-introduced ligand (including a ligand to receptor and a ligand to an enzyme), a biotin-introduced enzyme analogue, a biotin-introduced product prepared by introducing biotin into a substance of an original enzyme of an enzyme analogue, a biotin-introduced lectin, or a biotin-introduced sugar.

Furthermore, instead of the biotin-introduced enzyme, the present invention can be carried out, using other biotin-introduced labeling substances, such as a biotin-introduced fluorescent substance or a biotin-introduced fluorescent substance-binding protein, a biotin-introduced luminescent substance or a biotin-introduced luminescent substance-binding protein, or a biotin-introduced radioactive isotope.

EXAMPLES

The present invention now will be further illustrated by, but is by no means limited to, the following Examples.

Example 1

(1) Preparation of a Biotin-introduced Antibody Fragment Fab'

From an antiserum obtained from a rabbit immunized with human α-fetoprotein (AFP), a specific antibody IgG fraction was obtained by an affinity column chromatography using an AFP-immobilized Sepharose 4B.

To the specific antibody IgG fraction [0.1 mol/l acetate buffer (pH4.5)], 2% by weight of pepsin was added. The digestion was carried out in an incubator overnight at 37° C. to obtain an antibody fragment F(ab')$_2$ fraction having a molecular weight of 100,000 by a gel chromatography. The F(ab')$_2$ fraction was dyalized against a 50 mmol/l acetate buffer (pH5.0). To 5 mg (1 ml) of the dyalized F(ab')$_2$ fraction, 50 µl of a 0.25 mol/l 2-mercaptoethylamine [50 mmol/l acetate buffer (pH5.0)] was added. The reduction was carried out at 37° C. for 90 minutes. The resulting reaction mixture was applied to a Sephadex G-25 column (1.5×13 cm) which had been equilibrated with a 50 mmol/l phosphate buffer (pH7.0) containing 1 mmol/l ethylenediaminetetraacetic acid (EDTA), and then an antibody fragment Fab' fraction eluted in a void volume was pooled.

To the antibody fragment Fab' fraction, 0.4 mg of N-biotinoyl-N'-(6-maleimidehexanoyl)-hydrazide dissolved in 0.1 ml of dimethylformamide was added. The mixture was allowed to stand overnight at room temperature, and then applied to a Sephadex G-25 column (1.5×13 cm) which had been equilibrated with a physiological saline. A biotin-introduced antibody fragment Fab' eluted in a void volume was pooled.

(2) Preparation of a Crosslinked Streptoavidin

To 1 mg of purified streptoavidin dissolved in 1 ml of 0.1 mol/l phosphate buffer (pH7.0), 20 µl of a 1% glutaraldehyde solution [0.1 mol/l phosphate buffer (pH7.0)] was added. The whole was mixed and allowed to stand at 4° C. for 16 hours. To the reaction mixture, 20 µl of a 4 mg/ml sodium borohydride solution prepared with a 0.1 mol/l phosphate buffer (pH7.0) was added. The mixture was allowed to stand at room temperature for 4 hours to reduce the aldehyde. The reaction mixture was applied to a Sephadex G-25 column (1.5×15 cm) which had been equilibrated with a 0.3 mol/l NaCl solution. A crosslinked streptoavidin eluted in a void volume was pooled.

(3) Coating of an Anti-AFP Monoclonal Antibody

Into each well of a white 96-well plate, 100 µl of a anti-AFP monoclonal antibody (Oriental Yeast Co., Ltd.) adjusted to 5 µg/ml with a 50 mmol/l carbonate buffer (pH9.5) was poured. Coating was carried out with shaking at 37° C. for 2 hours, and then the wells were washed with a washing solution [20 mmol/l tris-HCl buffer (pH7.5) containing 0.1% Tween 20]. The plate was used in the following procedure.

(4) Preparation of an Enzyme-labeled Antibody

The biotin-introduced antibody fragment Fab' (a final concentration=0.1 µg/ml) prepared in Example 1 (1), the crosslinked streptoavidin (a final concentration=1.2 µg/ml) prepared in Example 1 (2), and a biotin-introduced luciferase-biotin acceptor fused protein (Kikkoman Cor.) (a final concentration=0.07 µg/ml) were mixed in a 50 mmol/l HEPES buffer (pH7.5) containing 5% glycerol, 1% bovine serum albumin (BSA), and 1 mmol/l EDTA, and the whole then allowed to stand at room temperature for 2 hours. The resulting mixture was used as an enzyme-labeled antibody in the following procedure.

(5) Measurement of AFP by an ELISA Method

Into each well coated with the antibodies, 100 µl of standard AFP solutions, which had been diluted to predetermined concentrations (1 pg/ml, 10 pg/ml, and 100 pg/ml) with a reaction buffer (the above-mentioned washing solution containing 0.15 mol/l NaCl) were poured, and the reaction then carried out with shaking at 37° C. for 1 hour. After washing the well with the washing solution four times, 100 µl of the enzyme-labeled antibody prepared in Example 1 (4) was poured into each well, and the reaction then carried out with shaking at 37° C. for 1 hour. After washing the well with the washing solution four times, the plate was placed in an emission detector. As a substance, 100 µl of a 50 mmol/l HEPES buffer (pH7.5) containing 0.2 mg/ml luciferin, 40 mmol/l ATP, and 150 mmol/l MgSO$_4$ was added, and then each of a cumulative amount of luminescence for 10 seconds was measured.

The results are shown in FIG. 1. As apparent from FIG. 1, the response of the amount of luminescence was obtained when the concentration of AFP was very low.

As described above, it was found that the biotin-introduced antibody fragment Fab' can be stably bound to the biotin-introduced enzyme, using streptoavidin treated with a crosslinking agent Comparative Example 1

Figure 2:
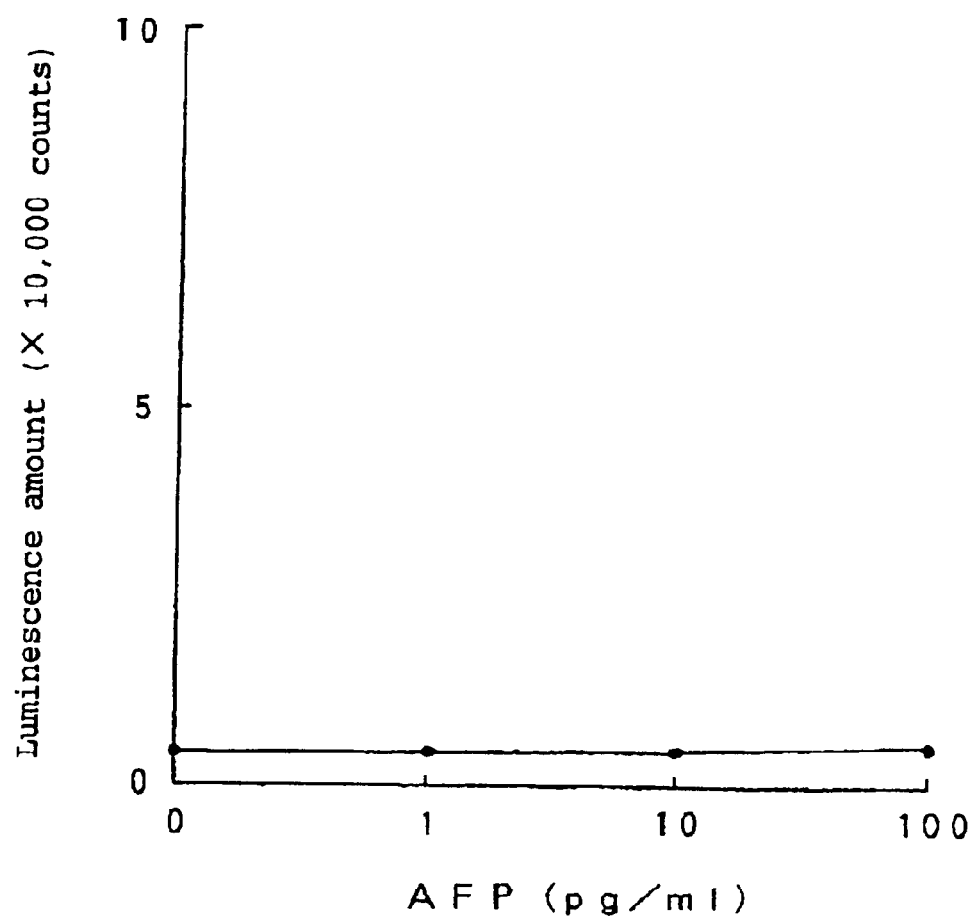
FIG. 2 is a graph showing the results obtained by measuring AFP in accordance with an ELISA using a non-crosslinked streptoavidin.

As a comparative Example, the procedure described in Example 1 (4) and Example 1 (5) was repeated except that streptoavidin without a crosslinking treatment was used instead of the crosslinked streptoavidin prepared in Example 1 (2). The results are shown in FIG. 2. As apparent from FIG. 2, little response of luminescence against an amount of AFP was obtained. It was found that, when the non-crosslinked streptoavidin was used, the biotin-introduced antibody fragment Fab' could not be bound to the biotin-introduced enzyme.

INDUSTRIAL APPLICABILITY

According to the present invention, a compound to be analyzed can be quickly, conveniently and accurately analyzed while taking advantage of the avidin-biotin reaction.

As above, the present invention was explained with reference to particular embodiments, but modifications and improvements obvious to those skilled in the art are included in the scope of the invention.

What is claimed is:

1. A biotin-avidin-biotin complex comprising at least two biotinylated substances which are the same or different, and a crosslinked avidin sandwiched therebetween, wherein said crosslinked avidin consists of an avidin monomer or an avidin polymer having intermolecular crosslinkages between two or more avidin monomers, wherein each of said avidin monomers has intramolecular crosslinkages between avidin subunits, and wherein only the avidin portion of the complex is crosslinked.

2. The biotin-avidin-biotin complex according to claim 1, wherein at least one of said biotinylated substances is a biotinylated binding component and at least one of said biotinylated substances is a biotinylated labeling substance.

3. A process for preparing said biotin-avidin-biotin complex according to claim 1, comprising the steps of:

(1) treating an avidin with a crosslinking agent to prepare a crosslinked avidin, wherein said crosslinked avidin consists of an avidin monomer or an avidin polymer having intermolecular crosslinkages between two or more avidin monomers, wherein each of said avidin monomers has intramolecular crosslinkages between avidin subunits, and wherein only the avidin portion of the complex is crosslinked;

(2) biotinylating the same or different substances to be biotinylated to prepare the same or different biotinylated substances; and (3) binding said crosslinked avidin and said same or different biotinylated substances to form said biotin-avidin-biotin complex according to claim 1.

4. A method for analyzing a compound to be analyzed, said method comprising the steps of:
   (1) providing a sample suspected of containing said compound to be analyzed;
   (2) bringing into contact sequentially and in any order said sample, a biotinylated binding component that specifically binds said compound, a crosslinked avidin, and a biotinylated labeling substance, to form a complex of said compound to be analyzed, said biotinylated binding component, said crosslinked avidin, and said biotinylated labeling substance, wherein said crosslinked avidin consists of an avidin monomer or an avidin polymer having intermolecular crosslinkages between two or more avidin monomers, wherein each of said avidin monomers has intramolecular crosslinkages between avidin subunits, and wherein only the avidin portion of the complex is crosslinked; and
   (3) analyzing a signal derived from said labeling substance in said complex.

5. The analyzing method according to claim 4, wherein said binding compound is selected from the group consisting of an antibody, an antibody fragment, an antigen, a DNA, an RNA, a receptor, a ligand to a receptor, an enzyme, a ligand to an enzyme, an enzyme analogue, a substrate for an enzyme which is an origin of an enzyme analogue, a lectin, and a sugar.

6. The analyzing method according to claim 5, wherein said antibody fragment is Fab'.

7. The analyzing method according to any one of claims 4 to 6, wherein said biotinylated labeling substance is selected from the group consisting of a biotinylated enzyme, a biotinylated fluorescent substance, a protein bound to a biotinylated fluorescent substance, a biotinylated luminescent substance, a protein bound to a biotinylated luminescent substance, and a biotinylated radioactive isotope.

8. The analyzing method according to claim 7, wherein said biotinylated enzyme is a fused protein of an enzyme and a biotinylated biotin acceptor.

9. The analyzing method according to claim 8, wherein said crosslinked avidin is selected from the group consisting of a crosslinked egg-white avidin, a crosslinked streptoavidin, and a crosslinked recombinant avidin.

10. The analyzing method according to claim 7, wherein said biotinylated enzyme is a biotinylated luciferase.

11. The analyzing method according to any one of claims 4 to 6, wherein said crosslinked avidin is selected from the group consisting of a crosslinked egg-white avidin, a crosslinked streptoavidin, and a crosslinked recombinant avidin.

12. The analyzing method according to claim 10, wherein said crosslinked avidin is selected from the group consisting of a crosslinked egg-white avidin, a crosslinked streptoavidin, and a crosslinked recombinant avidin.

13. The analyzing method according to claim 7, wherein said crosslinked avidin is selected from the group consisting of a crosslinked egg-white avidin, a crosslinked streptoavidin, and a crosslinked recombinant avidin.

14. An analyzing reagent comprising a mixture of:
   (1) a biotinylated binding component;
   (2) a crosslinked avidin, wherein said crosslinked avidin consists of an avidin monomer or an avidin polymer having intermolecular crosslinkages between two or more avidin monomers, wherein each of said avidin monomers has intramolecular crosslinkages between avidin subunits, and wherein only the avidin portion of the complex is crosslinked; and
   (3) a biotinylated labeling substance.

15. The analyzing reagent of claim 14, wherein said binding component is selected from the group consisting of an antibody, an antibody fragment, an antigen, a DNA, an RNA, a receptor, a ligand to a receptor, an enzyme, a ligand to an enzyme, an enzyme analogue, a substrate for an enzyme which is an origin of an enzyme analogue, a lectin, and a sugar.

16. The analyzing reagent of claim 15, wherein said antibody fragment is an Fab' fragment.

17. A method for analyzing a compound to be analyzed, said method comprising the steps of:
   (1) providing a sample suspected of containing said compound to be analyzed;
   (2) providing a biotin-avidin-biotin complex comprising a biotinylated binding component and a biotinylated labeling substance, and a crosslinked avidin sandwiched therebetween, wherein said crosslinked avidin consists of an avidin monomer or an avidin polymer having intermolecular crosslinkages between two or more avidin monomers, wherein each of said avidin monomers has intramolecular crosslinkages between avidin subunits, and wherein only the avidin portion of the complex is crosslinked;
   (3) bringing said into contact with said biotin-avidin-biotin complex to form a complex of said compound to be analyzed and said biotin-avidin-biotin complex; and
   (4) analyzing a signal derived from said labeling substance in said complex formed in step (3).

* * * * *